(12) United States Patent
Schostek et al.

(10) Patent No.: US 9,138,227 B2
(45) Date of Patent: Sep. 22, 2015

(54) IMPLANTING APPARATUS

(71) Applicant: Ovesco Endoscopy AG, Tuebingen (DE)

(72) Inventors: Sebastian Schostek, Tuebingen (DE); Stefan Zamida, Reutlingen/Betzingen (DE); Thomas Gottwald, Kochel am See (DE); Marc O. Schurr, Tuebingen (DE)

(73) Assignee: Ovesco Endoscopy AG, Tuebingen (DE)

( * ) Notice: Subject to any disclaimer, the term of this patent is extended or adjusted under 35 U.S.C. 154(b) by 286 days.

(21) Appl. No.: 13/682,025

(22) Filed: Nov. 20, 2012

(65) Prior Publication Data

US 2013/0144312 A1 Jun. 6, 2013

(30) Foreign Application Priority Data

Nov. 22, 2011 (EP) .................................... 11190135

(51) Int. Cl.
*A61B 17/10* (2006.01)
*A61B 17/122* (2006.01)
(Continued)

(52) U.S. Cl.
CPC .............. *A61B 17/10* (2013.01); *A61B 5/0084* (2013.01); *A61B 5/02042* (2013.01);
(Continued)

(58) Field of Classification Search
CPC .. A61B 17/10; A61B 17/128; A61B 17/1285; A61B 1/0014; A61B 1/00147; A61B 5/02042; A61B 5/6861; A61B 5/6879; A61B 5/688; A61B 5/6881; A61B 5/6882; A61B 5/6883; A61B 5/6884; A61B 2560/063; A61B 2560/066; A61B 5/0084; A61B 5/076; A61B 17/1227

USPC ................. 600/101, 104, 127, 129, 371, 373; 607/116, 126, 130, 179; 606/142, 151, 606/157, 158
See application file for complete search history.

(56) References Cited

U.S. PATENT DOCUMENTS 5,297,536 A * 3/1994 Wilk .............................. 600/104
5,406,418 A * 4/1995 Deary ........................... 359/827
(Continued)

FOREIGN PATENT DOCUMENTS

| EP | 1902660 A1 | 3/2008 |
|---|---|---|
| EP | 2163206 A1 | 3/2010 |
| WO | WO-2011066431 A2 | 6/2011 |

OTHER PUBLICATIONS

European Application Serial No. 11190135.1, European Search Report dated Apr. 25, 2012, 4 pgs.

*Primary Examiner* — Ryan Severson
*Assistant Examiner* — Christian Knauss
(74) *Attorney, Agent, or Firm* — RatnerPrestia (57) ABSTRACT

An endoscope-like implanting instrument includes an endoscope cap having a holding and withdrawing mechanism for a tissue clip adapted to be slipped onto an expanding sleeve of the endoscope cap. The endoscope cap has a front groove opening at the front edge of the sleeve. A withdrawing thread radially crosses the front groove at an axial front cap portion. The instrument further includes a tissue grasping mechanism being shiftably inserted into the working channel for manually grasping and drawing the tissue inside the endoscope cap. A clamping mechanism is integrally arranged inside the endoscope cap in axial extension to the working channel, holding a capsule-like device and connected with the tissue clip via a thread, band or string such that the capsule-like device will be automatically detached by the grasping mechanism when being manually actuated for tissue grasping.

11 Claims, 9 Drawing Sheets

(51) Int. Cl.
*A61B 17/128* (2006.01)
*A61B 5/00* (2006.01)
*A61B 5/02* (2006.01)
*A61B 5/07* (2006.01)

(52) U.S. Cl.
CPC ............ *A61B 5/6861* (2013.01); *A61B 5/6884* (2013.01); *A61B 17/1227* (2013.01); *A61B 17/1285* (2013.01); *A61B 5/076* (2013.01); *A61B 2560/066* (2013.01)

(56) References Cited

U.S. PATENT DOCUMENTS

| | | | | |
|---|---|---|---|---|
| 6,285,897 | B1 * | 9/2001 | Kilcoyne et al. | 600/350 |
| 6,352,503 | B1 * | 3/2002 | Matsui et al. | 600/104 |
| 6,689,056 | B1 * | 2/2004 | Kilcoyne et al. | 600/300 |
| 6,849,078 | B2 * | 2/2005 | Durgin et al. | 606/142 |
| 6,911,032 | B2 * | 6/2005 | Jugenheimer et al. | 606/142 |
| 7,076,305 | B2 * | 7/2006 | Imran et al. | 607/40 |
| 7,235,089 | B1 * | 6/2007 | McGuckin, Jr. | 606/167 |
| 7,448,993 | B2 * | 11/2008 | Yokoi et al. | 600/114 |
| 7,828,730 | B2 * | 11/2010 | Schostek et al. | 600/371 |
| 2002/0032454 | A1 * | 3/2002 | Durgin et al. | 606/151 |
| 2002/0055750 | A1 * | 5/2002 | Durgin et al. | 606/151 |
| 2002/0103424 | A1 * | 8/2002 | Swoyer et al. | 600/350 |
| 2003/0013938 | A1 * | 1/2003 | Iddan et al. | 600/129 |
| 2003/0139647 | A1 * | 7/2003 | Raz et al. | 600/104 |
| 2004/0133089 | A1 * | 7/2004 | Kilcoyne et al. | 600/350 |
| 2005/0043601 | A1 * | 2/2005 | Kilcoyne et al. | 600/361 |
| 2005/0165272 | A1 * | 7/2005 | Okada et al. | 600/114 |
| 2005/0240202 | A1 * | 10/2005 | Shennib et al. | 606/142 |
| 2006/0074457 | A1 * | 4/2006 | Imran et al. | 607/40 |
| 2007/0049796 | A1 * | 3/2007 | Fujikura | 600/116 |
| 2007/0093858 | A1 * | 4/2007 | Gambale et al. | 606/142 |
| 2007/0203395 | A1 * | 8/2007 | Mikkaichi | 600/127 |
| 2007/0260112 | A1 * | 11/2007 | Rahmani | 600/104 |
| 2008/0065169 | A1 * | 3/2008 | Colliou et al. | 607/40 |
| 2008/0097182 | A1 * | 4/2008 | Schostek et al. | 600/371 |
| 2008/0117291 | A1 * | 5/2008 | Hirakawa et al. | 348/65 |
| 2009/0018396 | A1 * | 1/2009 | Takizawa et al. | 600/127 |
| 2009/0149870 | A1 * | 6/2009 | Jugenheimer et al. | 606/142 |
| 2011/0152888 | A1 * | 6/2011 | Ho et al. | 606/143 |
| 2011/0190578 | A1 * | 8/2011 | Ho et al. | 600/104 |
| 2011/0208210 | A1 * | 8/2011 | Baur et al. | 606/142 |

\* cited by examiner

Fig. 1

PRIOR ART

IMPLANTING APPARATUS

CROSS REFERENCE TO RELATED APPLICATIONS

This application claims priority under 35 U.S.C. §119 to European Application No. EP 11 190 135.1, filed Nov. 22, 2011, the content of which is incorporated by reference herein in its entirety and for all purposes.

FIELD

The present invention relates to an apparatus or instrument for at least temporarily implanting capsule-like metering, diagnose and/or monitoring devices, for example blood detection devices or the like, preferably in hollow organs of a human or animal body using a tissue clip.

BACKGROUND

From the state of the art, for instance according to U.S. Pat. No. 6,849,078 B2, a tissue clip of this species is generally known as regards its basic design. For a better comprehension, this tissue clip is described hereinafter in detail with reference to FIG. 1.

Figure 1:
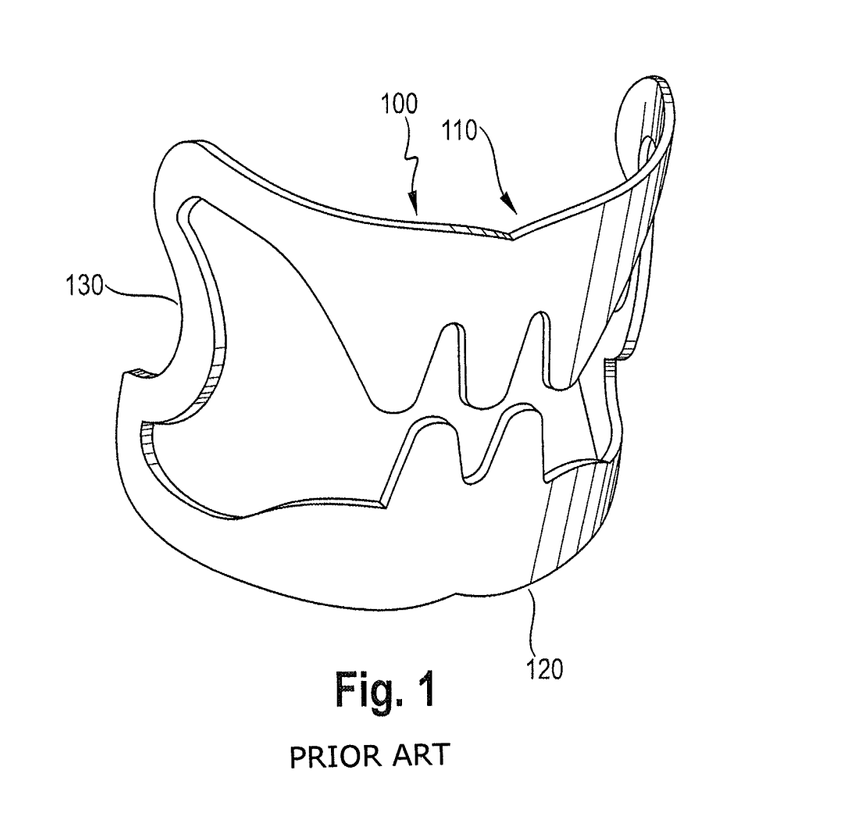
FIG. 1 shows the exemplary design of a tissue clip as it is known already from the state of the art and as it is equally employed in the present invention.

Accordingly, such a clip 100 consists of a mouth-type clamping means having two toothed jaws 110, 120 adapted to be opened and shut via two lateral hinges 130 or by flexible moldings. The hinges 130 or the flexible moldings are preferably formed of spring-elastic straps which during opening the jaws 110, 120 store spring energy which results in a snapping of the jaws 110, 120 at a predetermined clamping force when the jaws 110, 120 are released, i.e. when the hinges 130 or the flexible moldings are actuated.

In detail, each clip 100 is punched in one piece out of a spring steel sheet by working a ring having a partially different ring width out of the spring steel sheet. Two diametrically opposed ring portions having a large ring width constitute the two jaws 110, 120, whereas the two ring portions disposed there between having a narrow ring width form the hinges 130 or the flexible moldings. The jaws 110, 120 are formed by arching the ring portions having a large ring width in a curved shape, wherein the two ring portions having a narrow ring width are twisted about their longitudinal axis by approximately 180° in order to form the hinges. This special shaping of the punched out spring steel sheet creates the shape of a type of shark mouth having two rows of teeth moving toward each other which are formed by punching out the ring portions having a large ring width.

The functioning of the afore-described medical tissue clip 100 can be described as follows:

In general, an endoscopic implantation of a medical device in total constitutes the most tolerable process for the patient. In this case the medical device must be fixed from the inside of a hollow organ to the latter. For this purpose, a number of the afore-described tissue cleats, clips or anchors are inserted into the hollow organ by means of an endoscope and are positioned at predetermined positions at the inner face of the organ. To this end, the respective clip or anchor is brought close to the organ tissue and the biasing spring is released for snapping of the clip or clamping of the anchor. The latter then clamps or holds a tissue fold between its jaws or its hooks or needles at a predetermined clamping or expanding force, wherein the teeth, hooks, needles or jags of each jaw cut into the tissue and preferably penetrate the same. In this way the clips or anchors are anchored to the inner face of the organ at predetermined spaces and thus form introducing points into the organ tissue for a tensile force.

The endoscope not shown in detail in FIG. 1 usually is equipped with an endoscope head or an endoscope cap which includes, apart from the functions generally required for an endoscope such as lighting, optical system and rinsing means, if necessary, in addition a holding and withdrawing means for the tissue clip. This holding and withdrawing means substantially consists of an expanding sleeve as well as a slide operable manually or by remote control which is movable in the longitudinal direction of the endoscope. The expanding sleeve is configured such that the already opened tissue clip can be attached to the sleeve in such manner that the clip can be prevented from slipping backwards while being inserted into the hollow organ. For this purpose, the slide is positioned axially behind the clip and serves so-to-speak as an axial stop for the clip.

As soon as the clip is to be positioned at a particular site, the slide is moved axially forward and in so doing strips off the clip over the expanding sleeve. Accordingly, the clip is actuated, i.e. the biasing mechanism within the clip described before by way of FIG. 1 is released when the latter is stripped off the expanding sleeve and the two jaws of the tissue clip snap to close while clamping the tissue provided there between.

Besides, for example the reference US 2008/0097182 A1 discloses a device for hemorrhage detection being adapted to ensure a continuous monitoring of bleeding within a hollow organ of a human patient which device uses a tissue clip according to the above description for fixing the device at the inner wall of the hollow organ. The known device will be described in the following text portion with reference to FIG. 9.

Figure 9:
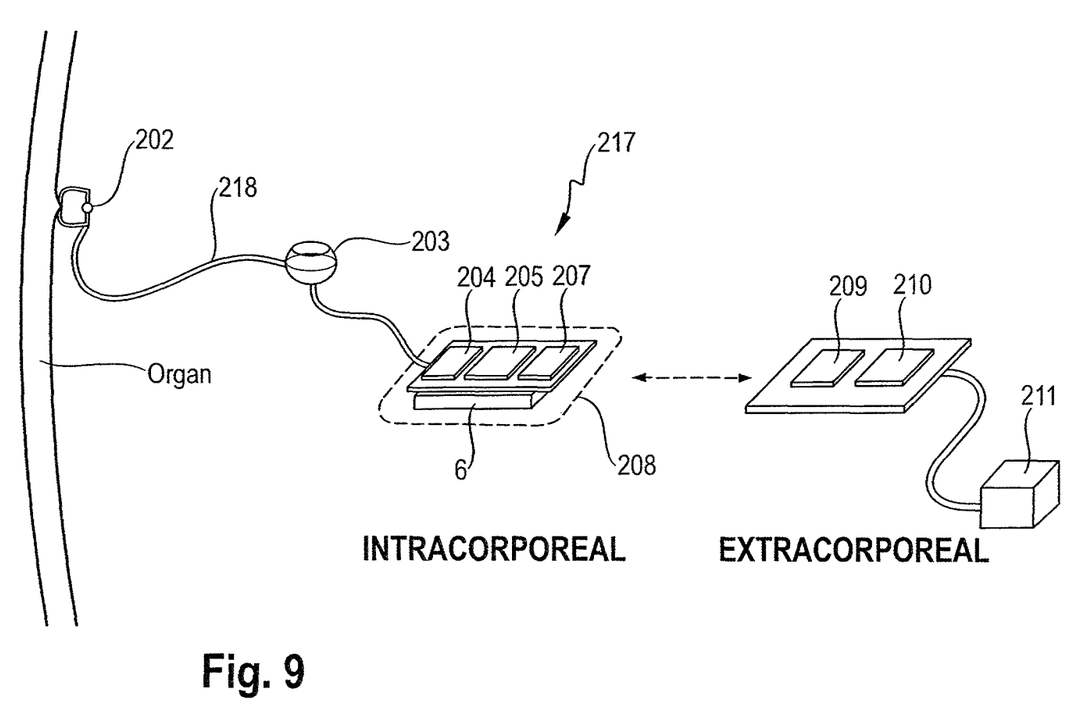
FIG. 9 illustrates in principle a blood detection system comprising a blood detecting capsule as can be used in the present implanting instrument.

As may be gathered from FIG. 9, the device for hemorrhage detection is basically composed of an intracorporeal part and an extracorporeal part. Hereinafter, the intracorporeal part shall be described first. The intracorporeal part comprises a fixing member 202, which is a clip or anchor in this embodiment and which is mounted to an inner wall of the hollow organ, the digestive tract in this embodiment. A detecting means 203 is connected to the clip 202 via a connecting member 218, e.g. a cord or the like. In this embodiment, the detecting means 203 is composed of two light sources, one of which emits light in the UV range, and the other emits light in the red range of the visible spectrum, and a photosensitive sensor, such as a photodiode or a phototransistor. In a pulsed manner or successively, the light sources emit light into the interior of the hollow organ in which the light is absorbed and reflected, and the photosensitive sensor detects the light transmitted or reflected in the interior. The fixing means 202 can be formed as a stent-like structure or as a clip according to the above description. In this embodiment, the fixing means 202 is adapted to mount/fix the detecting means 203 in a tubular hollow organ, e.g. in the duodenum, for monitoring diffuse bleeding sources in the stomach or in the esophagus. The connecting member 218 for connecting the detecting means 203 to the fixing member 202 may be formed as a cord, a wire or the like. In an embodiment, the connecting member 218 is adapted to be made of a decomposing material, e.g. a biodegradable material, which decomposes gradually. Depending on the organ and the application, the decomposition time is set such that the connecting member 218 separates the fixing member 202 from the detecting means 203 only after, preferably directly after, a reasonable observation time has elapsed. This measure permits the detecting means 203 to be excreted naturally through the digestive tract, separately from the fixing member 202. The detecting means 203 is connected to a transmitting unit 217 by means of a data transmitting cable, so that signals are transmissible between the photosensitive sensor and the transmitting unit 217. Alternatively, the detecting means may be anchored in the transmitting unit 217 or may be unitarily formed therewith. The transmitting unit 217 is basically composed of a data processing unit 204, an analog-digital converter 205, an energy source 206, e.g. a battery, and a transmitter 207. The data processing unit 204 controls the detecting means 203, the analog-digital converter 205 and the transmitter 207, and evaluates the data received by the photosensitive sensor. The analog-digital converter 205 converts the analog signals sent by the detecting means 203 into digital signals, and the transmitter 207 forwards the data evaluated by the data processing unit 204 to a receiving unit 209. The data transmitted by the transmitter 207 may be e.g. measured values, status information or event signals, e.g. the event of the occurrence of a bleeding. In this embodiment, the transmitting unit 217 is surrounded by an encapsulation 208, in order to protect the elements of the transmitting unit 217. In one example, the encapsulation is formed of a body-compatible material. The extracorporeal part is basically composed of a receiving unit 209, an interface 210, and an evaluation unit 211. The receiving unit 209 receives data sent by the transmitter 207 via a wireless transmission. The data received by the receiving unit in this way are adapted to be evaluated or represented in an evaluating unit 211 may e.g. be an optical device or an acoustic signaling device, such as a display or a loudspeaker. Furthermore, the data received by the receiving unit are transmissible by means of the interface 210 to third parties, e.g. a doctor or an emergency hotline/center. Hereinafter, the function of the device for hemorrhage detection shall now be described. The intracorporeal part composed of anchor 202, detecting means 203 and transmitting unit 217 is introduced into the digestive tract by means of an endoscope. There, the anchor 202 is fixed to an inner wall of the digestive tract by means of the endoscope. Thus, the detecting means 203 and the transmitting unit 217 are fixed in the interior of the digestive tract by the anchor 202. There, the detecting means 203 detects whether there is any blood in the digestive tract, or not. This works as follows: the two light sources of the detecting means 203, which emit light at a predetermined wavelength, are controlled by the receiving unit 204 such that each light source emits light successively, the one light source emits light in the UV range, and the other light source emits light in the red range of the visible spectrum. The light emitted by the light sources emerges into the interior of the digestive tract, and is absorbed or reflected by the contents in the interior. The photosensitive sensor in the form of a photodiode or phototransistor, formed in the detecting means 203, detects the light transmitted or reflected in the interior of the digestive tract, and produces a sensor signal on the basis of the detected light. Thus, one sensor signal is generated for each light source. If there is any blood in the interior of the digestive tract, the light emitted by the light sources in absorbed differently, as if there is no blood in the digestive tract, since blood has a specific characteristic absorption spectrum that differs from the absorption spectrum of the "normal" organ contents. Accordingly, the light reflected in the interior and received by the photosensitive sensor dependence on the presence of blood in the interior of the organ and, accordingly, also the sensor signals that are sent out by the photosensitive sensor are different depending on the presence or absence of blood. Thus, due to the different sensor signals of the photosensitive sensor, the presence or absence of blood may be detected.

In practice, it turned out, that especially the insertion action of a capsule-like device of this kind into the hollow organ using an endoscopic instrument creates problems in so far as, on the one hand, the capsule-like device has to be held inside the endoscopic instrument such it will not unintentionally be stripped off when being inserted into the hollow organ. On the other hand, however, for a smooth positioning action at the inner wall of the hollow organ the capsule-like device has to be disconnected from the endoscopic device in a simple manner wherein the function of the above-mentioned clip and of the endoscopic device itself should not be affected.

For example, the WO 2011/066431 discloses a wireless capsule-like device being endoscopically anchored to the bowel wall using an endoscopic clip. In this implementation, the capsule-like device is designed to be integral part of the endoscopic clip with a minimum dimension on the 3 mm-scale in order to be introduced through the working channel of an endoscope into the hollow organ of the body.

A technical drawback of this solution is that the form factor is not compatible with currently commercially available battery technology, as the smallest button cell available has an outer diameter of 4.8 mm (e.g. Type 337 battery sold under the trademark Energizer®). Furthermore, it is known that for telemetric data transmission the antenna configuration inside the capsule-like device benefits from being surrounded by isolating material such as a plastic mold creating a distance to electrolytes such as biological tissue. In other words, an implementation of the capsule-like device in which the antenna is physically close to biological tissue surrounding the capsule-like device leads to significant damping effects on the electromagnetic waves being emitted from the antenna. Thus, for an appropriate signal strength outside the body, high output power may be necessary, which on the other hand may lead to undesired effects on the surrounding tissue.

For this reason, capsule-like wireless devices for monitoring of parameters such as the detection of bleeding, an embodiment with minimum outer dimensions in the range of at least 5 mm is technologically advantageous. However, the implantation through the working channel of an endoscope, which is usually in the 3 mm range, is not possible. On the other hand, with endoscopic delivery devices such as the delivery device sold by US Endoscopy, Ohio, USA under the trademark AdvanCE®, it is possible to deliver capsule-like devices with outer diameter in the range of at least 5 mm into a hollow organ of the body. These type of devices, however, do not have the capability of anchoring the capsule-like device to the wall of the hollow organ.

An integral endoscopic implanting apparatus which offers both the possibility of safe and easy introduction as well as secure anchoring of the capsule-like device of this kind is not known at present.

For this reason, it is desirable to provide an implanting apparatus or instrument for at least temporarily implanting a capsule-like device using a clip as a fixing means, wherein said implanting apparatus or instrument allows a safe insertion of the capsule-like device into a hollow organ of, for example, a human patient and a smooth disconnection of the capsule-like device when the clip gets fixed at the hollow organ.

SUMMARY

The drawbacks of known apparatuses and instruments are addressed by an implanting apparatus or instrument having the technical features according to the present invention.

Accordingly, the endoscope-like implanting instrument may include an endoscope cap comprising a holding and withdrawing means for a tissue clip especially in accordance with the above description being slipped onto an expanding sleeve of the endoscope cap. Furthermore, the endoscope cap may have a (manual) clip actuating means for slipping the tissue clip off the expanding sleeve. The actuating means may comprise a front groove-like opening at the front edge of the expanding sleeve slitting open the cap sheath wall on both sides (or in other words, the front groove opens to both sides in circumferential direction at the outer circumference of the expanding sleeve thereby forming a tongue-like axial projection), as well as a withdrawing thread or string radially crossing the front groove-like opening at an axial front cap portion substantially in radial direction and being fixedly connected to the tongue-like projection at its one end and being movably introduced or adapted to be introduced into an endoscope channel forming a working channel or being separate to a working channel of the instrument for manually operating the same at a radial inner face of the endoscope cap.

Therefore, in case a clip is slipped onto the expanding sleeve and enters the gap between the sleeve wall and the tongue-like projection the crossing thread or string will be pulled by the clip getting a curved elongation within the gap. If the thread or spring is now manually actuated the curved elongation within the gap gets straightened thereby slipping the clip off the expanding sleeve.

Alternative to the fixation of the thread or spring at the tongue-like projection, the thread or string might be connected at its distal end to a pushing ring, moveably/shiftably supported on the expanding sleeve (having no tongue-like axial projection) such that when the thread or string is manually actuated (pulled) the radial outer pushing ring is pulled along the expanding cap in direction to the distal end portion thereof, thereby slipping the clip (being in front of the pushing ring) off the expanding cap. Besides it is also possible to provide a pushing bar or pushing cable within the working channel or a separate functional channel which is connected at its distal end with the pushing sleeve or ring to apply a pushing force thereto for shifting the clip off the expanding cap.

Finally, the endoscope-like implanting instrument may be adapted to receive or comprise a surgical instrument being shiftably fed within the working channel of the implanting instrument, for example a tissue grasping means being moveably or shiftably inserted into the working channel for manually grasping and drawing the tissue of the hollow organ inside the endoscope cap, to bring and hold it in a position such that the tissue clip can be brought into clamping connection with the tissue when the clip is slipped off the expanding sleeve.

According to the invention, the implanting instrument may additionally include a holding means, especially a clamping means integrally arranged inside the endoscope cap, especially inside the expansion or expanding sleeve in an axial (distal) extension to the working channel (that means, axially in front of the working channel), such that the holding or clamping means being located axially in front of the working channel with an axial distance between the holding/clamping means and the distal opening of the working channel. The holding/clamping means holds (or is adapted to hold) a capsule-like device such as a metering (for example a drug delivery means), diagnose and/or monitoring device, for example a blood detection device according to the above description being connected with the tissue clip especially of the above-mentioned design via a thread, band or string such that the capsule-like device will be automatically detached from the clamping means directly or indirectly by the surgical instrument, for example the grasping means when being manually actuated, for example for tissue grasping. This means, that a separate tool for detaching the capsule-like device (besides the surgical instrument) is not needed. Furthermore, directly and indirectly means that the surgical instrument may directly contact the capsule-like device or will contact a kind of a firing means like a lever system or a spring to fire the capsule-like device.

Because, according to one aspect of the invention, the holding/clamping means may be located inside the expanding sleeve, the capsule-like device attached thereto is protected by the expanding sleeve when being inserted into the hollow organ. Additionally, because according to another aspect of the invention the clamping means may be located in front of the working channel with a predetermined axial distance there between the capsule-like device does not need to enter the working channel when being clamped so that the working channel is not needed to get radial enlarged. Therefore, the function of the surgical instrument, for example the grasping means, can be maintained.

The clamping means according to a further aspect of the invention may be dimensioned such that the clamping force applied to the capsule-like device is high enough to safely hold the capsule-like device when it is (will be) inserted/shifted into the hollow organ. The clamping force, however, is weak enough to allow a disconnection of the capsule-like device from the clamping means by the surgical instrument, for example the grasping means in case the surgical instrument is shifted forward into the distal direction of the implanting instrument. Therefore, the surgical instrument, especially the grasping means generally in the form of a bit hook, needle or the like, connected to a pushing cable/rod fed inside the working channel is not needed to get additionally enforced to achieve a sufficient pushing force onto the capsule-like device for its disconnection.

In order to enhance this disconnection action, the clamping means according to another aspect of the invention is designed such that its disconnection direction is axial or co-axial to the shifting direction of the surgical instrument. Therefore, in case the surgical instrument is shifted forward out of the working channel it automatically contacts the capsule-like device for pushing it out of the clamping means.

According to a further aspect of the invention, the clamping means is designed as a ring having a specific elasticity to get radial expanded when the capsule is inserted, thereby applying a predetermined radial clamping force onto the capsule-like device. To improve the elastic character of the clamping means the ring is not formed as a closed but as an open ring having two arc-shaped arms forming a ring gap there between. Here, it has to be pointed out, that the implanting device is equipped with an optic having a lens system or a light sensitive chip at the distal end thereof inside the expanding sleeve/endoscope cap. According to another aspect of the invention, the above open ring is orientated such that the ring gap is substantially in front of the optic to allow a free view to the distal direction of the instrument.

According to a further aspect of the present invention the clamping means is integrally connected to the endoscope cap/expanding sleeve, for example by resin molding, gluing, melting or the like, and can be made of the same or different material with respect to the expanding sleeve. The interconnection between the clamping means in the form of an open ring and the expanding sleeve is substantially point- or line-shaped along a predetermined distance in circumferential direction such that the elastic movement of the free two ring arms and the clamping force exclusively generated by the ring arms are not affected.

Finally, it shall be clarified that the above aspects can be claimed separately as being individual solutions of the cited object but also in combination with each other in accordance with the enclosed claim combinations.

BRIEF DESCRIPTION OF THE DRAWINGS

Hereinafter, the invention is explained in detail by way of a preferred embodiments with reference to the accompanying drawings, in which.

DETAILED DESCRIPTION OF EMBODIMENTS

Figure 2:
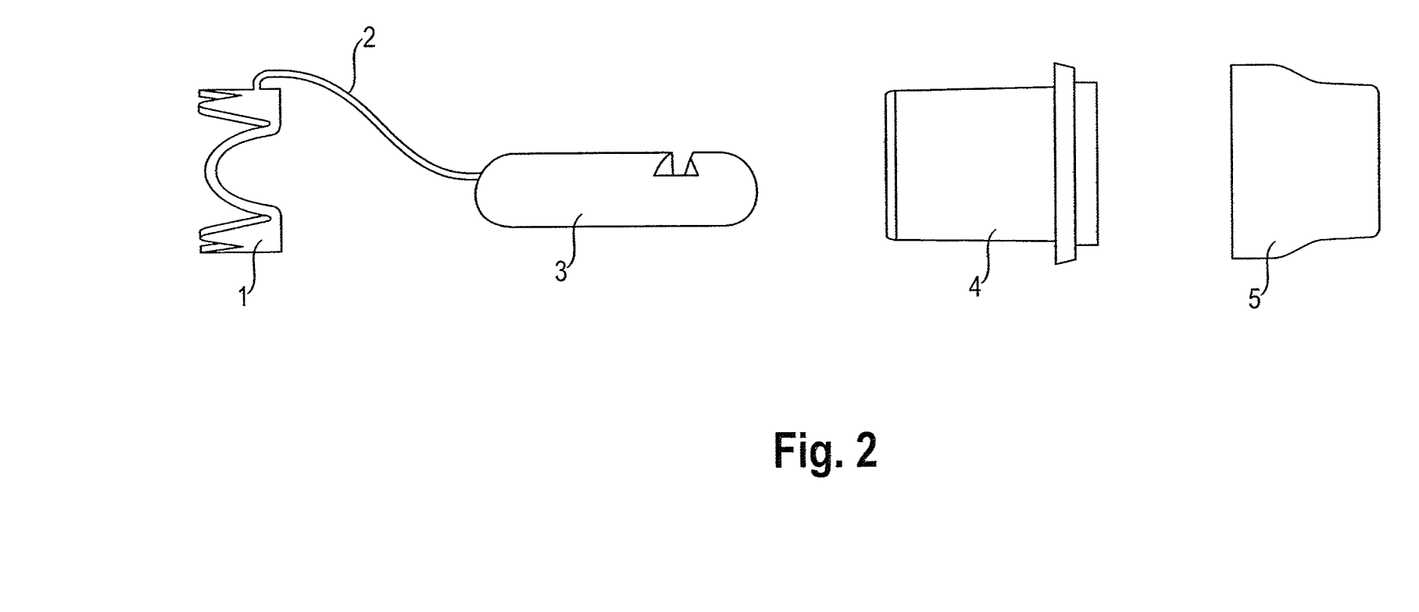
FIG. 2 illustrates an exploded view of an capsule-like device (especially a blood detecting capsule) being interconnected with a tissue clip by a thread or string, an expansion cap and a connection adapter of an endoscope-like instrument.
Figure 3A:
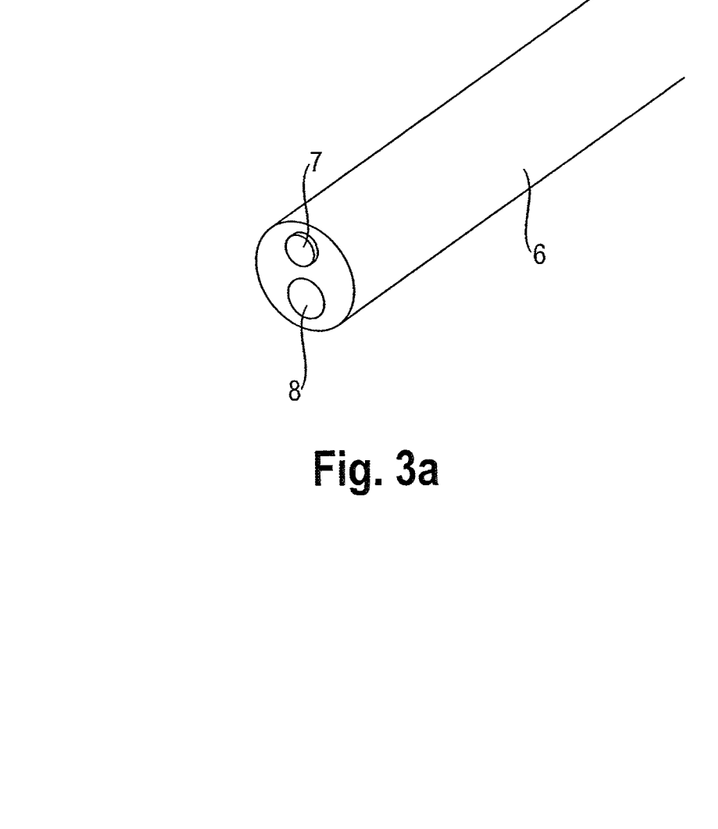
FIGS. 3a and 3b show the distal end portion of the endoscope-like instrument comprising at least a working channel feeding a surgical instrument having an instrument end effector especially a grasping means for tissue grasping and an optic, like a lens-system and/or a photosensitive chip.
Figure 3B:
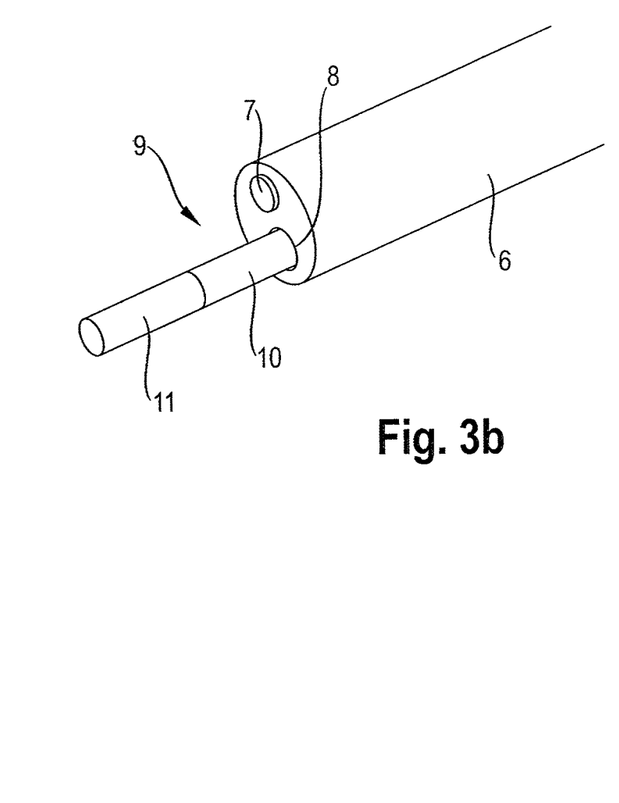

According to FIGS. 2, 3a and 3b, the endoscope-like implanting instrument according to a preferred embodiment of the invention comprises an endoscope or endoscope shaft 6 having a proximal end portion (not shown) with an actuation handle and a distal end at which an optic 7 preferably comprising a lens system and/or a light sensitive chip (CMOS or CCD chip) is located. Inside the endoscope shaft 6 at least one working channel 8 is formed in which a surgical instrument, for example a tissue grasping means 10, 11 is supported such that is can be manually actuated at the proximal handle at least for moving/shifting along the working channel 8, The surgical instrument has a distal end effector 11, for example a hook, a needle or a forceps, which is operably connected to an instrument shaft or cable 10 capable of transmitting actuating forces from the handle to the end effector 11.

At the distal end of the endoscope shaft 6 an adapter piece (cap fixation) 5 in the form of a bushing or sleeve is fixedly (integrally) connected or mounted with the endoscope shaft 6 wherein at the distal end of the adapter piece 5 and an expanding sleeve 4 is placed/formed. The expanding sleeve 4 has an outer circumferential surface adapted to spread a tissue clip 1 (as known from the prior art) when it will be slipped onto the expanding sleeve 4.

Figure 4:
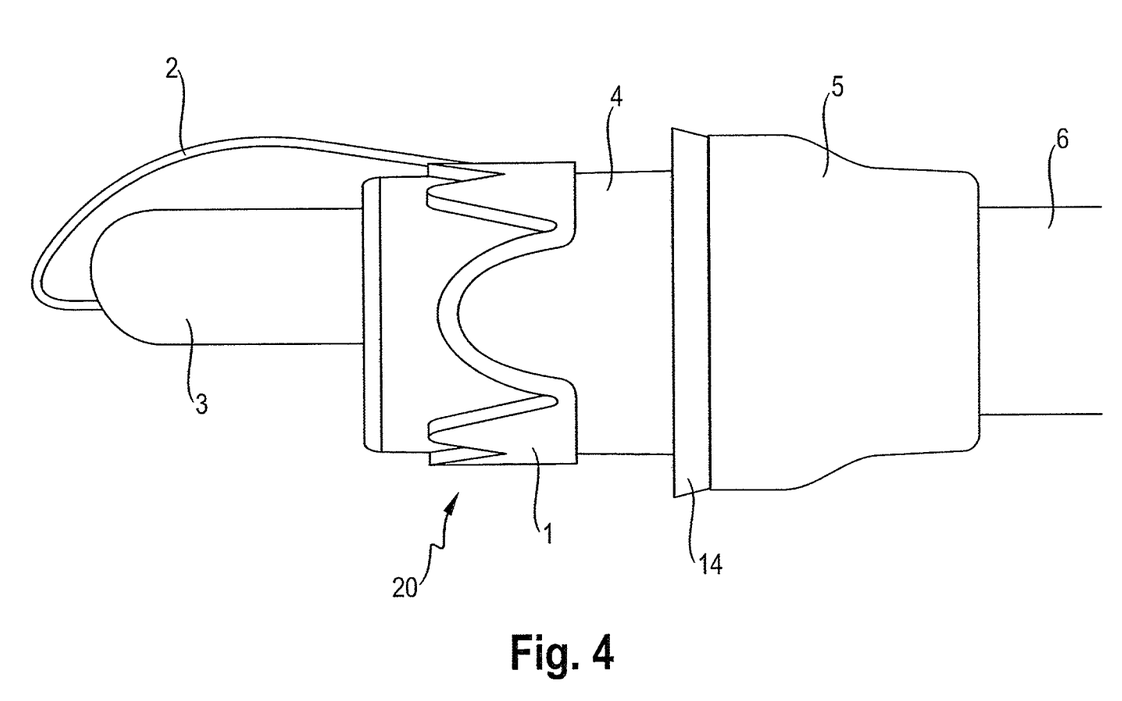
FIG. 4 illustrates the endoscope-like implanting instrument in a fully mounted state for getting inserted into a hollow organ, comprising the endoscope and the expansion cap carrying the tissue clip and the capsule-like device.
Figure 5A:
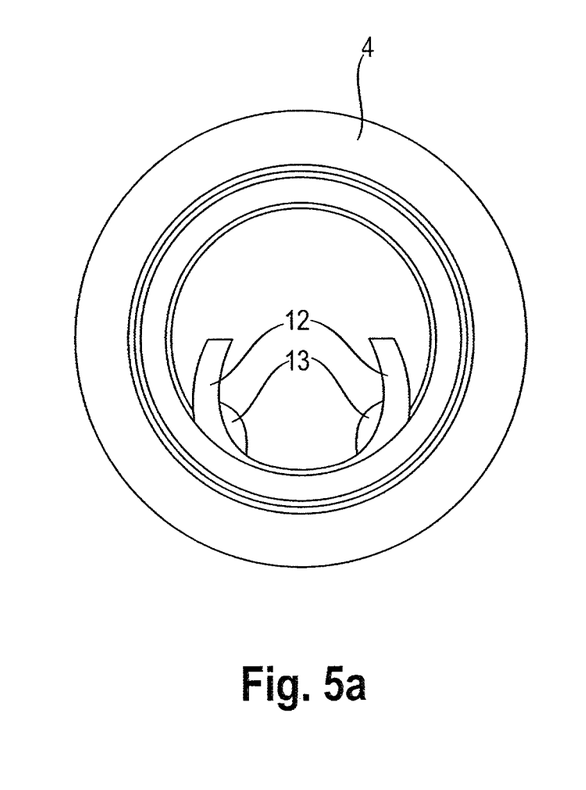
FIGS. 5a and 5b show the front view of the expanding cap having the clamping means for holding the capsule-like device also in relation with the working channel and the optic of the endoscope.
Figure 5B:
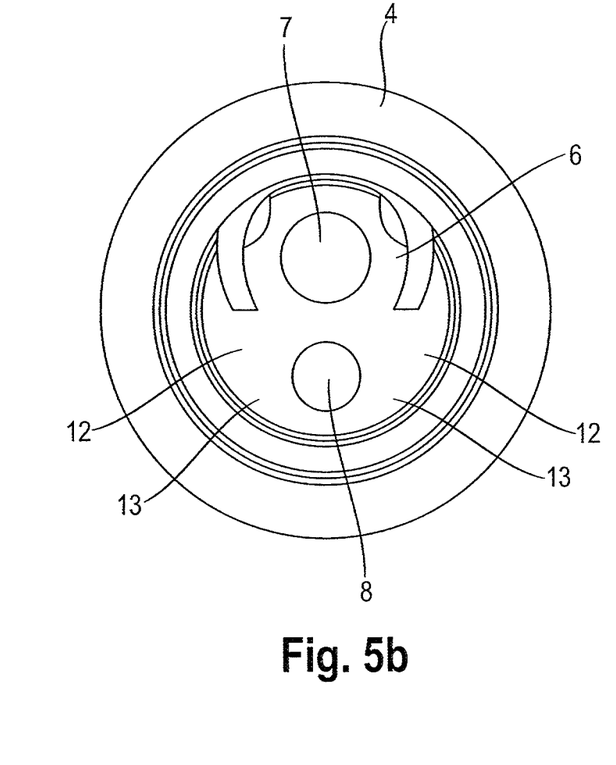

For example, in FIG. 4 the endoscope-like inserting or implanting instrument in a fully mounted state is shown. Accordingly, the tissue clip 1 is already slipped onto the expanding sleeve 4 such that it has its clip mouth elastically opened wherein a shifting ring 14 is located between the adapter piece 5 and the tissue clip 1. The shifting ring 14 is moveably supported on the expanding sleeve 4 and is coupled with a withdrawing thread or string (not shown in the drawings but well known in the prior art) entering the expanding sleeve 4 and the working channel 8 or a specific feeding channel (not shown) parallel to the working channel 8, feeding the withdrawing thread to the proximal handle.

As can be seen in FIGS. 5a, 5b, 6a, 6b and 7, the expanding sleeve 4 is equipped with a clamping means 12, 13 comprising an open ring or a longitudinally slit bushing 12 which is located inside the expanding sleeve 4 axially in front of (distal to) the opening of the working channel 8. As shown especially in FIG. 6a, the open ring 12 is positioned such that a predetermined axial distance between the open ring 12 and the distal end side (having the opening of the working channel 8) of the endoscope shaft 6 is maintained. Furthermore, the open ring 12 is orientated such that the ring gap of the open ring 12 is positioned in front of (close to) the optic 7, such that the front view of the optic 7 will be not or only minimally affected by the open ring 12. In other words, the open ring 12 is located substantially axial or co-axial in front of the working channel 8 wherein the ring gap is directed to the optical axis of the optic 7. Finally, within the axial distance between the ring 12 and the distal end side of the endoscope shaft 6 an implant position means in the form of two radial projections 13 (see FIGS. 6a and 8) are formed defining an axial end position for an implant when being clipped in the clamping means.

Figure 6A:
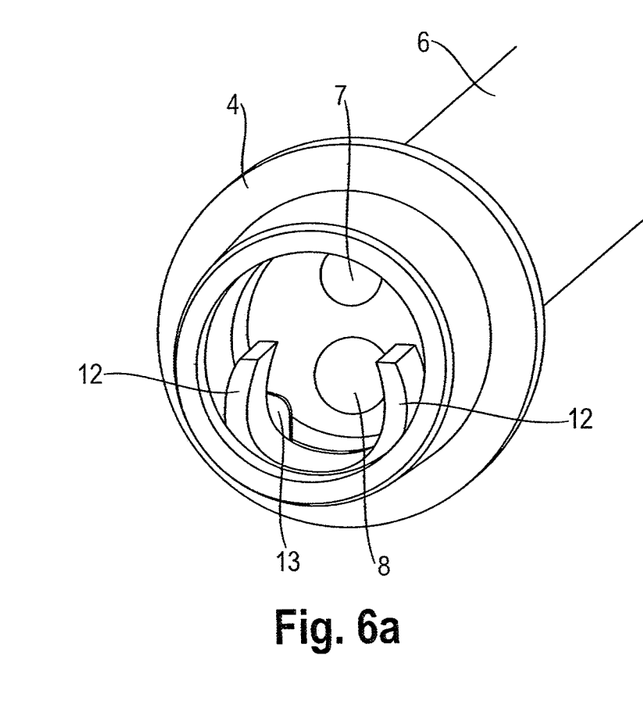
FIGS. 6a and 6b show perspective views of the expanding cap without and with the capsule-like device held by the clamping means.
Figure 6B:
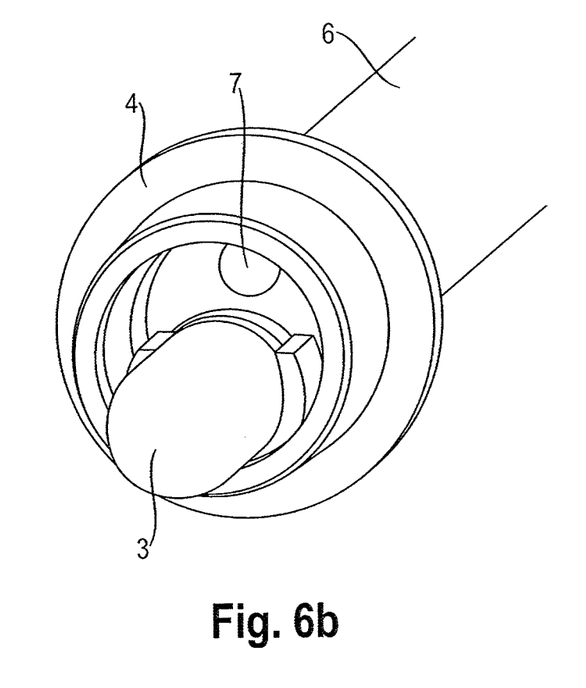

According to FIG. 2, the above implant of the present embodiment is a capsuled blood detection device 3 of a well known design having a cartridge-like casing with an outer circumferential diameter larger than the inner diameter of the open ring 12 such that when being clipped inside the ring 12 as shown in FIG. 6b the open ring 12 (or its ring arms) get elastically widened so that a predetermined clamping force is applied to the capsuled device 3. The capsuled device 3 is connected with the tissue clip 1 by a connection thread or string 2 as shown in FIG. 4. However it is also possible that the implant is a metering capsule or just a tablet for successively supplying a drug to the patient's organ.

The function of the endoscope-like implanting instrument having the above basic design will be described in the following:

As already stated above, FIG. 4 shows the inventive implanting instrument in a fully mounted state. Here, the tissue clip 1 is slipped onto the expanding sleeve wherein the capsule-like device 3 being interconnected with the clip 1 by the connection thread 2 is clamped by the open ring (clamping means) 12. As can be best seen in FIG. 6b, the implant positioning means 13 provide an axial end stopper for the implant 3 such that the implant is held by the open ring 12 in front of (distal) the working channel 8 without entering the working channel 8. In this mounting state the implanting instrument is ready to get inserted into a hollow organ of a patient. Because the implant 3 is shielded by the surrounding expanding sleeve 4 the insertion movement of the implanting instrument can smoothly be done without the risk of losing the implant 3.

Figure 7:
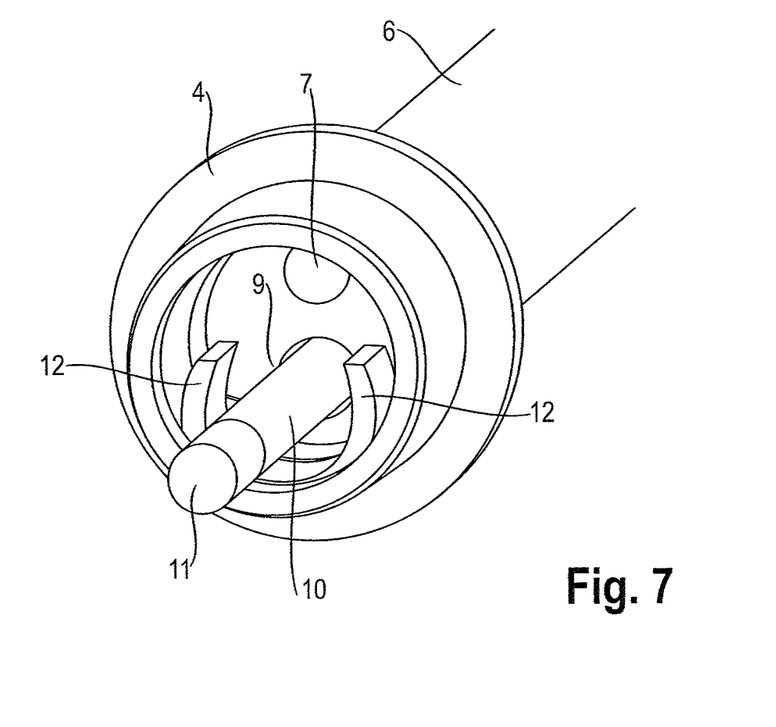
FIG. 7 shows the expanding cap with the surgical instrument (grasping means) being ascended from the working channel.
Figure 8:
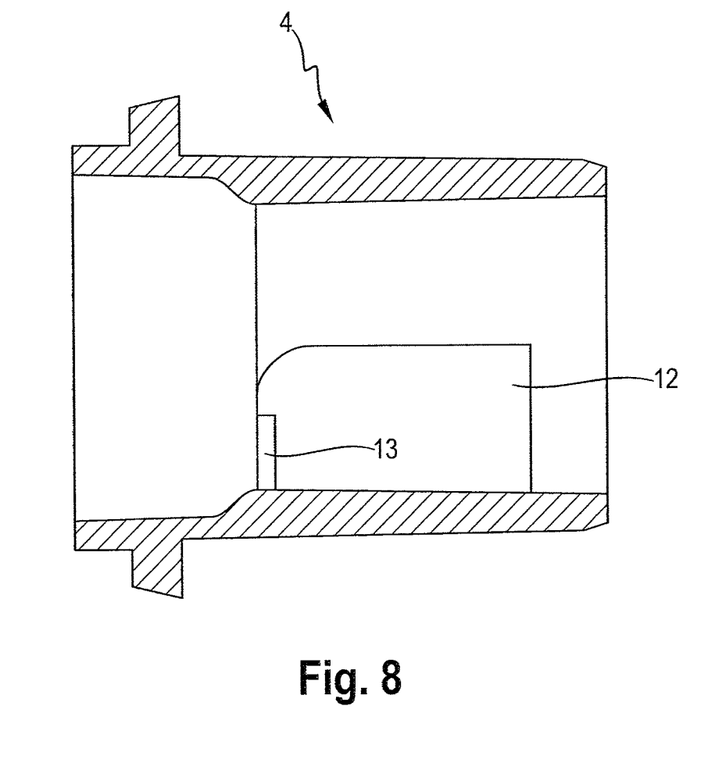
FIG. 8 illustrates a longitudinal cross section of the expanding cap.

In case the implanting instrument has reached its end position within the hollow organ the surgical instrument 10, 11 is actuated by forward shifting. In other words, in case the surgical instrument 10, 11, for example a tissue gripping means is shifted outward of the working channel 8 it hits the capsuled device 3 being clipped in the open ring 12. Because the central axis of the ring 12 is axial or at least co-axial with the working channel 8 at its distal end portion the surgical instrument 10, 11 easily starts to shift the capsuled device 3 out of the ring 12 as it is shown in FIG. 7.

Finally, the withdrawing thread (not shown) for actuating the tissue clip 1 is pulled at the proximal end of the endoscope shaft 6 so that the pushing ring 14 is pulled forward in the direction to the tissue clip 1. Thereby the tissue clip 1 gets slowly moved forward until it slips off the expanding sleeve 4 to grasp tissue of the hollow organ and to fix the capsuled implant 3 at the selected position.

What is claimed:

1. An endoscope-like implanting instrument having an endoscope cap unit for holding and withdrawing a tissue clip slipped onto an expanding sleeve of the endoscope cap unit, said endoscope cap unit comprises a clip actuating means for slipping the tissue clip off the expanding sleeve, said clip actuating means has a withdrawing thread or string or a pushing bar or pushing cable that is movably introduced or adapted to be introduced into an endoscope channel forming a working channel or separate to the working channel of the endoscope-like implanting instrument for manually operating the clip actuating means at a proximal end portion of the endoscope-like implanting instrument to slip off the tissue clip from the expanding sleeve wherein said endoscope-like implanting instrument is adapted to receive a surgical instrument that is shiftably inserted into the working channel for axially deploying from the distal end of the working channel when manually actuated, wherein a holding or clamping means is integrally arranged inside the endoscope cap unit, the clamping means holding a capsule-like device connected with the tissue clip via a connection thread, band or string, such that the capsule-like device will be automatically detached directly or indirectly by said surgical instrument when manually actuated.

2. An endoscope-like implanting instrument according to claim 1, wherein said clamping means is arranged inside the endoscope cap unit such that the clamping means is located axially in front of the working channel or a distal opening with an axial distance therebetween.

3. An endoscope-like implanting instrument according to claim 1, wherein said capsule-like device is a metering, diagnosis and/or monitoring device.

4. An endoscope-like implanting instrument according to claim 1, wherein said clamping means is dimensioned such that a clamping force applied to the capsule-like device is high enough to safely hold the capsule-like device when the capsule-like device is inserted into the hollow organ, but weak enough to allow a disconnection of the capsule-like device from the clamping means by the surgical instrument when the surgical instrument is shifted forward in the distal direction of the endoscope-like implanting instrument.

5. An endoscope-like implanting instrument according to claim 1, wherein said clamping means is designed such that a disconnection direction of the clamping means is axial or co-axial to a shifting direction of the surgical instrument.

6. An endoscope-like implanting instrument according to claim 1, wherein said clamping means is designed as a ring that is radially expanded by the capsule-like device, the ring having a specific elasticity to apply a predetermined radial clamping force onto the capsule-like device.

7. An endoscope-like implanting instrument according to claim 6, wherein said ring is formed as an open ring having two arc-shaped arms forming a ring gap therebetween.

8. An endoscope-like implanting instrument according to claim 7, wherein the endoscope-like implanting device is equipped with an optic having a lens system or a light sensitive chip at the distal end of the endoscope-like implanting device inside the endoscope cap unit, wherein the open ring is orientated such that the ring gap is substantially in front of the optic to allow a free view in a distal direction of the endoscope-like implanting instrument.

9. An endoscope-like implanting instrument according to claim 8, wherein the clamping means is in the form of an open ring is interconnected to an interior portion of the expanding sleeve at a portion of the open ring away from the ring gap.

10. An endoscope-like implanting instrument according to claim 1, wherein said clamping means is integrally connected with the endoscope cap unit by resin molding, gluing, or melting and can be made of the same or different material with respect to the expanding sleeve.

11. An endoscope-like implanting instrument according to claim 1, wherein said surgical instrument forms an exchangeable or freely selectable part of the endoscope-like implanting instrument.

* * * * *